United States Patent
Yoshida et al.

(10) Patent No.: US 10,293,003 B2
(45) Date of Patent: May 21, 2019

(54) MULTILINEAGE-DIFFERENTIATING STRESS ENDURING (MUSE) CELLS FOR TREATMENT OF CHRONIC KIDNEY DISEASE

(71) Applicants: CLIO, INC., Akita-shi, Akita (JP); TOHOKU UNIVERSITY, Sendai-shi, Miyagi (JP)

(72) Inventors: Masanori Yoshida, Akita (JP); Mari Dezawa, Sendai (JP)

(73) Assignees: CLIO, INC., Akita-shi, Akita (JP); TOHOKU UNIVERSITY, Sendai-shi, Miyagi (JP)

(*) Notice: Subject to any disclaimer, the term of this patent is extended or adjusted under 35 U.S.C. 154(b) by 0 days.

(21) Appl. No.: 15/413,129

(22) Filed: Jan. 23, 2017

(65) Prior Publication Data

US 2017/0128498 A1    May 11, 2017

Related U.S. Application Data

(63) Continuation of application No. 14/695,872, filed on Apr. 24, 2015, now abandoned.

(30) Foreign Application Priority Data

Feb. 26, 2014   (JP) ................. 2014-035931

(51) Int. Cl.
*A61K 35/545* (2015.01)
(52) U.S. Cl.
CPC ................. *A61K 35/545* (2013.01)
(58) Field of Classification Search
CPC .................................................. A61K 35/545
See application file for complete search history.

(56) References Cited

U.S. PATENT DOCUMENTS

2007/0178071 A1* 8/2007 Westenfelder ......... A61K 35/22
   424/93.7
2011/0070647 A1* 3/2011 Dezawa ............... C12N 5/0607
   435/378

FOREIGN PATENT DOCUMENTS

WO    2011/007900 A1    1/2011

OTHER PUBLICATIONS

Kuroda et al. "Unique multipotent cells in adult human mesenchymal cell populations" PNAS May 11, 2010. (Year: 2010).*
Yang et al. "Isolation and characterization of SSEA3(+) stem cells derived from goat skin fibroblasts."Cell Reprogram. Jun. 2013;15(3):195-205. (Year: 2013).*
Simerman et al. "Pluripotent muse cells derived from human adipose tissue: a new perspective on regenerative medicine and cell therapy." ClinTransl Med. May 22, 2014;3:12. (Year: 2014).*
Kuroda, Yasumasa et al., "Unique multipotent cells in adult human mesenchymal cell populations," *PNAS* (May 11, 2010), 107(19):8639-8643.
Kuroda, Yasumasa et al., "Isolation, culture and evaluation of multilineage-differentiating stress-enduring (Muse) cells," *Nature Protocols* (published online Jun. 20, 2013); 8(7):1391-1415.
Li, Shaoyi et al., "Bystander effect-mediated gene therapy of gliomas using genetically engineered neural stem cells," *Cancer Gene Therapy* (published online Mar. 18, 2005); 12:600-607.
Morton, Michael J. et al., "Human Podocytes Possess a Stretch-Sensitive, $Ca^{2+}$-Activated $K^+$Channel: Potential Implications for the Control of Glomerular Filtration," *J. Am. Soc. Nephrol.* (Accepted Aug. 24, 2004); 15:2981-2987.
Mundel, Peter et al., "Podocyte Biology and Response to Injury," *J. Am. Soc. Nephrol.* (Dec. 2002); 13:3005-3015.
Pavenstädt, Hermann et al., "Cell Biology of the Glomerular Podocyte," *Physiol. Rev.* (Jan. 2003); 83:253-307.
Schmid, Holger et al., "Gene Expression Profiles of Podocyte-Associated Molecules as Diagnostic Markers in Acquired Proteinuric Diseases," *J. Am. Soc. Nephrol.* (Accepted Jul. 19, 2003); 14:2958-2966.
Li et al, "Isogenic mesenchymal stem cells transplantation improves a rat model of chronic aristolochic acid nephropathy via upregulation of hepatic growth factor and downregulation of transforming growth factor β1," Mol. Cell Biochem., 2012, vol. 368, pp. 137-145.
"Therapeutic Potential of Adipose-Derived Stem Cells for anti-GBM Glomerulonephritis," Inflammation and Regeneration, Jul. 2010, vol. 30, No. 4 (76), p. 360.
Tohoku Igaku Zasshi, 2013, vol. 125, pp. 107-109.
Izawa, M., "Newly discovered multipotent stem cell Muse cells derived from human organism: Possibility for nerve regeneration medicine," Peripheral Nerve, vol. 23, No. 2, 2012, pp. 135-139.

* cited by examiner

*Primary Examiner* — Titilayo Moloye
(74) *Attorney, Agent, or Firm* — Kilpatrick Townsend & Stockton LLP

(57) ABSTRACT

An object of the present invention is to provide a novel medical application to regenerative medicine that uses pluripotent stem cells (Muse cells). The present invention provides a cell preparation for treating chronic kidney disease that contains SSEA-3-positive pluripotent stem cells isolated from mesenchymal tissue in the body or cultured mesenchymal cells. The cell preparation of the present invention is based on a renal tissue regeneration mechanism by which Muse cells are made to selectively accumulate at a site of kidney disease and differentiate into cells that compose the kidney by administering Muse cells intravenously to a subject having the aforementioned disease.

7 Claims, 10 Drawing Sheets bar=50μm

FIG. 10
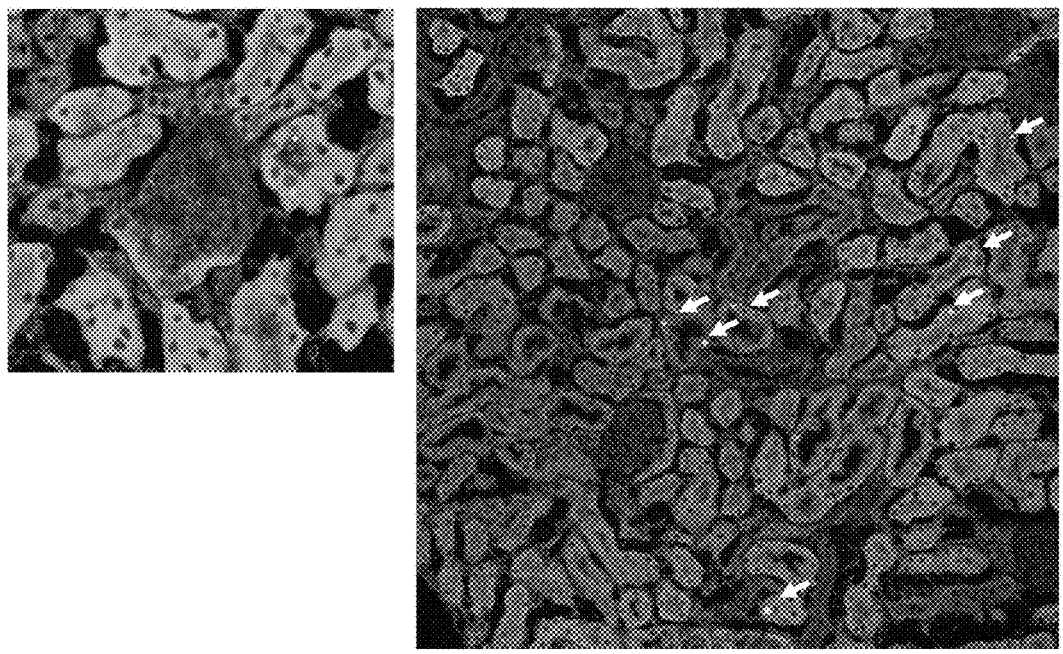
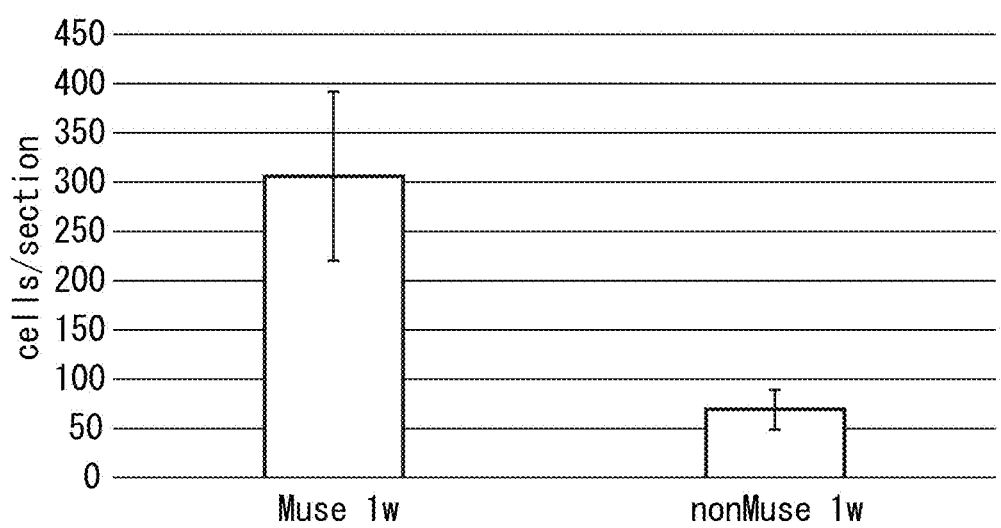

MULTILINEAGE-DIFFERENTIATING STRESS ENDURING (MUSE) CELLS FOR TREATMENT OF CHRONIC KIDNEY DISEASE

CROSS-REFERENCE TO RELATED APPLICATIONS

The current application is a continuation of U.S. patent application Ser. No. 14/695,872, filed Apr. 24, 2015, pending, which application claims priority to JP 2014-035931, filed Feb. 26, 2014, the disclosures of which are hereby incorporated by reference in their entireties for all purposes.

FIELD OF INVENTION

The present invention relates to a cell preparation used in regenerative medicine. More specifically, the present invention relates to a cell preparation containing pluripotent stem cells that are effective for repairing and regenerating renal tissue that has been damaged by renal failure.

BACKGROUND OF THE INVENTION

The increase in the number of patients going on dialysis in recent years is creating problems in terms of both patient QOL and national medical care expenditures. In the case of many chronic kidney diseases, including chronic glomerular nephritis, diabetic nephropathy and polycystic kidney disease, the course of the disease is progressive, and unless treatment is effective, these diseases ultimately result in loss of kidney function, eventually leading to dialysis due to renal failure. At present, dialysis treatment costs for treating kidney diseases (renal failure) exceeds one trillion yen, accounting for roughly 3% of all medical care expenditures, and the number of patients suffering from kidney damage is increasing annually. There are currently roughly 300,000 to 400,000 artificial dialysis patients in Japan, and medical costs required to undergo dialysis treatment for one month are said to be about 400,000 yen in the case of outpatient hemodialysis and 350,000 to 700,000 yen in the case of continuous ambulatory peritoneal dialysis (CAPD).

Among kidney diseases, glomerular epithelial cell disorders refer to disorders in which the glomerular epithelium is subjected to functional or structural damage due to various causes. Here, glomerular epithelial cells are referred to as podocytes, and are highly differentiated cells that line the outer surface of the glomerular basement membrane (GEM). Podocytes are a determinate component of the filtration barrier, and mutations in the genes of nephrin, podocin, α-actinin-4 and the like have been found to cause kidney disease-associated proteinuria (Schmid, H., et al., J. Am. Soc. Nephrol., Vol. 14, p. 2958-2966 (2003); Mundel, P. & Shankland, S. J., J. Am. Soc. Nephrol., Vol. 13, p. 3005-3015 (2002)). In addition, podocytes regulate glomerular filtration rate in response to changes in perfusion pressure by reacting to changes in pressure in glomerular capillaries (Mundel, P., et al., 2002, supra; Morton, M. J., J. Am. Soc. Nephrol., Vol. 15, p. 2981-2987 (2004); Pavenstadt, H., et al., Physiol. Rev., Vol. 83, p. 253-307 (2003)). In this manner, since glomerular epithelium containing podocytes fulfills an important role in the waste filtration function of the kidneys, it is imperative to prevent disorders of the glomerular epithelium from progressing to renal sclerosis so as not to allow further increases in the number of dialysis patients.

On the other hand, kidney diseases are not limited to disorders of the glomerulus, but also include diseases affecting renal tubules. Renal tubules are formed from the proximal renal tubule, the loop of Henle, the distal renal tubule and the renal collecting duct. If an abnormality occurs in the function of the renal tubules for some reason, various diseases may occur throughout the body. Examples of diseases of the proximal renal tubule include Fanconi's syndrome, aminoaciduria and renal glycosuria, while distal renal tubular acidosis is known to be a typical example of a disease of the distal renal tubule.

As chronic kidney disease progresses, since the functions possessed by a normal kidney are lost, effects extend to various organs throughout the body, typically resulting in uremia. Specific examples of disorders that occur include central nervous system disorders, peripheral nervous system disorders, cardiovascular disorders, gastrointestinal disorders, vision/ophthalmic disorders, blood/coagulation disorders, immune disorders, endocrine disorders, skin disorders, bone/joint disorders, electrolyte disorders and acid-base balance disorders. In these cases, artificial dialysis for preventing uremia is essential for the treatment of chronic kidney diseases, and kidney transplant is the only radical treatment that ensures a complete recovery. However, it is impossible for all patients with chronic kidney diseases to undergo kidney transplant due to a shortage of donors. Ever since dialysis treatment was first performed on patients with kidney diseases in the 1920s, there has yet to be developed a treatment method that places a reduced burden on the patient.

It has been determined from research by M. Dezawa, one of the inventors of the present invention, that multilineage-differentiating stress enduring cells (Muse cells) expressing surface antigen in the form of stage-specific embryonic antigen-3 (SSEA-3), which are present in mesenchymal cell fractions and can be obtained without going through an induction procedure, are responsible for the pluripotency possessed by mesenchymal cell fractions, and that they have the potential for application to disease treatment aimed at tissue regeneration. In addition, Muse cells were also determined to be able to be concentrated by stimulating mesenchymal cell fractions with various types of stress (WO2011/007900; Li, S., et al., Cancer Gene Therapy, Vol. 12, p. 600-607 (2005); Kuroda, Y., et al., Proc. Natl. Acad. Sci. USA, Vol. 107, p. 8639-8643 (2010); Wakao, S., et al., Proc. Natl. Acad. Sci. USA, Vol. 108, p. 9875-9880 (2011); Kuroda, Y., et al., Nat. Protoco., Vol. 8, p. 1391-1415 (2013)). However, there have yet to be any examples of the use of Muse cells for the prevention and/or treatment of kidney disease, and the obtaining of anticipated therapeutic effects has yet to be clearly determined.

SUMMARY

An object of the present invention is to provide a novel medical application to regenerative medicine that uses pluripotent stem cells (Muse cells). More specifically, an object of the present invention is to provide a cell preparation for prevention and/or treatment of chronic kidney disease that contains Muse cells.

The inventors of the present invention found that intravascular administration of Muse cells into chronic kidney disease mice resulted in Muse cells accumulating in renal tissue, reconstruction and repair of damaged glomeruli and renal tubules and improvement or recovery of renal function, thereby leading to completion of the present invention.

Namely, the present invention is as described below.

[1] A cell preparation for preventing and/or treating chronic kidney disease, containing pluripotent stem cells positive for SSEA-3 isolated from biological mesenchymal tissue or cultured mesenchymal cells.

[2] The cell preparation according to [1] above, wherein the pluripotent stem cells positive for SSEA-3 contain a concentrated cell fraction as a result of stimulation by external stress.

[3] The cell preparation according to [1] and [2] above, wherein the chronic kidney disease is selected from the group consisting of chronic glomerular nephritis, renal sclerosis, diabetic nephropathy, renal cyst, chronic pyelonephritis, rapidly progressive glomerulonephritis, malignant hypertension, SLE nephritis, renal amyloidosis, renal/urinary tract tumors, myeloma, obstructive uropathy, renal gout, renal hypoplasia and renal/urinary tract tuberculosis.

[4] The cell preparation according to [1] to [3] above, wherein the pluripotent stem cells are CD105-positive.

[5] The cell preparation according to [1] to [4] above, wherein the pluripotent stem cells are CD117-negative and CD146-negative.

[6] The cell preparation according to [1] to [5] above, wherein the pluripotent stem cells are CD117-negative, CD146-negative, NG2-negative, CD34-negative, vWF-negative and CD271-negative.

[7] The cell preparation according to [1] to [6] above, wherein the pluripotent stem cells are CD34-negative, CD117-negative, CD146-negative, CD271-negative, NG2-negative, vWF-negative, Sox10-negative, Snail-negative, Slug-negative, Tyrp1-negative and Dct-negative.

[8] The cell preparation according to [1] to [7] above, wherein the pluripotent stem cells are pluripotent stem cells having all of the properties indicated below:
(i) low or absent telomerase activity;
(ii) ability to differentiate into any of the three germ layers;
(iii) absence of demonstration of neoplastic proliferation; and,
(iv) self-renewal ability.

[9] The cell preparation according to [1] to [8] above, wherein the pluripotent stem cells have the ability to accumulate at the site of kidney disease.

[10] The cell preparation according to [1] to [9] above, wherein the pluripotent stem cells have the ability to differentiate into one or more cells selected from the group consisting of foot cells, mesangium cells, glomerular endothelial cells, juxtaglomerular cell, proximal tubular cells, distal tubular cells, vascular endothelial cells, Henle's loop, and/or collecting tubule cells.

The present invention is able to repress progression of chronic kidney disorder and improve kidney function by means of a renal tissue regeneration mechanism by which Muse cells are made to selectively accumulate in damaged renal tissue and differentiate into cells constituting renal tissue following their administration into a vein or the like of a subject suffering from chronic kidney disease.

BRIEF DESCRIPTION OF THE DRAWINGS

FIG. 5 indicates fluorescent images of regions containing a single glomerulus and the periphery thereof (after six weeks). Human Muse cell dose groups are shown in both the upper and lower rows of images. In the left panels, human Muse cells and non-Muse cells that took to mouse kidneys were detected using anti-human Golgi complex antibody. The center panels indicate autofluorescence of renal tissue. The right panels indicated fluorescent images obtained by subtracting fluorescence of the center panels from fluorescence of the left panels. As indicated by the arrows, Muse cells were widely distributed in renal tissue and took to glomeruli, renal tubules, interstitium and the like.

FIG. 10 indicates fluorescent images used to examine the mobility of non-Muse cells in the same manner as FIG. 9. Non-Muse cells were only observed in renal tubules and interstitium. In addition, the mobility of human Muse cells and non-Muse cells is indicated in the form of a graph (n=4 each).

DETAILED DESCRIPTION

Figure 1:
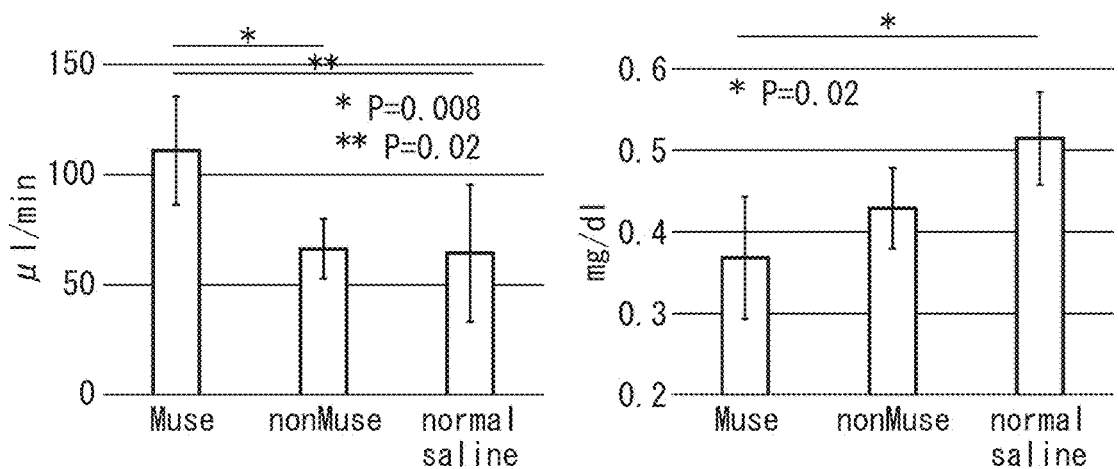
FIG. 1 indicates the results of evaluating renal function in a chronic kidney disease mouse (Balb/c) model six weeks after transplanting human Muse cells. The graph on the left indicates the results for creatinine clearance (μl/min), while the graph on the right indicates the results for serum creatinine (mg/dl). In the case of measurement of creatinine clearance, the function of the kidneys responsible for excretion of creatinine in the blood recovered significantly in the case of having administered Muse cells in comparison with dose groups administered non-Muse cells and physiological saline. In the case of measurement of serum creatinine, the serum creatinine concentration in a dose group administered Muse cells was lower in comparison with a dose group administered physiological saline, and that difference was statistically significant. On the other hand, a dose group administered non-Muse cells did not demonstrate a statistically significant difference in comparison with the physiological saline dose group.

The present invention relates to a cell preparation for preventing and/or treating chronic kidney disease that contains SSEA-3-positive pluripotent stem cells (Muse cells). The following provides a detailed explanation of the present invention.

1. Applicable Diseases

The present invention aims to prevent and/or treat chronic kidney disease using a cell preparation containing SSEA-3-positive pluripotent stem cells (Muse cells). Here, "chronic kidney disease" refers to all forms of pathological states, dysfunction or damage to kidneys that occur over a long period of time (such as several weeks, several months, several years or several tens of years) in which renal tubular cell function or glomerular filtration rate (GFR) continuously decreases and results in the onset of disease during that time. However, the present invention is not intended to eradicate kidney disease that occurs in a short period of time (such as several minutes, several hours or several days) in the manner of acute renal failure as an applicable disease thereof. Thus, according to the present invention, applicable diseases thereof may be considered to be chronic or acute diseases in tissue such as the glomeruli and renal tubules. Although there are no particular limitations thereon, examples of chronic kidney diseases include chronic glomerular nephritis, renal sclerosis, diabetic nephropathy, renal cyst, chronic pyelonephritis, rapidly progressive glomerulonephritis, malignant hypertension, SLE nephritis, renal amyloidosis, renal/urinary tract tumors, myeloma, obstructive uropathy, renal gout, renal hypoplasia and renal/urinary tract tuberculosis.

2. Cell Preparation (1) Pluripotent Stem Cells (Muse Cells)

The existence of the pluripotent stem cells used in the cell preparation of the present invention in the body was discovered by M. Dezawa, one of the applicants of the present invention, and the cells were named "multilineage-differentiating stress enduring (Muse) cells". Muse cells can be obtained from bone marrow, adipose tissue (Ogura, F., et al., Stem Cells Dev., Nov. 20, 2013 (Epub) (published on Jan. 17, 2014), or skin tissue such as dermal connective tissue, and are sporadically present in the connective tissue of various organs. In addition, these cells have both the properties of pluripotent stem cells and mesenchymal stem cells, and are identified as being double-positive for each of the cell surface markers of pluripotent stem cells, "stage-specific embryonic antigen-3 (SSEA-3)" and of mesenchymal stem cells such as "CD105". Thus, Muse cells or cell populations containing Muse cells can be isolated from body tissue, for example, by using these antigen markers as indicators. Details regarding methods used to isolate and identify Muse cells as well as their characteristics are disclosed in International Publication No. WO2011/007900. In addition, as has been reported by Wakao, et al. (2011, previously cited), in the case of using a cell culture obtained by culturing mesenchymal cells present in bone marrow, skin and the like as the parent population of Muse cells, all cells positive for SSEA-3 are known to be positive for CD105. Thus, in the cell preparation of the present invention, in the case of isolating Muse cells from biological mesenchymal tissue or cultured mesenchymal cells, Muse cells can be purified and used simply by using SSEA-3 as an antigen marker. Furthermore, in the present description, pluripotent stem cells (Muse cells) able to be used in a cell preparation for treating chronic kidney disease that have been isolated from biological mesenchymal tissue or cultured mesenchymal cells by using SSEA-3 as an antigen marker, or a cell population containing Muse cells, may simply be described as "SSEA-3-positive cells". In addition, In the present specification, "non-Muse cells" means cells included in biological mesenchymal tissue or cultured mesenchymal cells, which are not "SSEA-3-positive cells."

Simply speaking, Muse cells or cell populations containing Muse cells can be isolated from biological tissue (such as mesenchymal tissue) using antibody to the cell surface marker SSEA-3 alone or using antibody to SSEA-3 and CD105, respectively. Here, "biological tissue" refers to the biological tissue of a mammal. In the present invention, although an embryo in a development stage prior to a fertilized egg or blastula stage is not included in biological tissue, an embryo in a development stage in or after the fetus or blastula stage, including the blastula, is included. Examples of mammals include, but are not limited to, primates such as humans or monkeys, rodents such as mice, rats, rabbits or guinea pigs as well as cats, dogs, sheep, pigs, cows, horses, donkeys, goats and ferrets. The Muse cells used in the cell preparation of the present invention are clearly distinguished from embryonic stem (ES) cells and embryonic germ (EG) cells in that they are directly collectable from biological tissue and are non-tumorigenic. In addition, "mesenchymal tissue" refers to tissue such as bone, synovial membrane, fat, blood, bone marrow, skeletal muscle, dermis, ligaments, tendons, tooth pulp, umbilical cord, umbilical cord blood, as well as tissues present in various organs. For example, Muse cells can be obtained from bone marrow, skin or fat tissue. For example, Muse cells are preferably used that have been isolated from mesenchymal tissue collected from the living body. In addition, Muse cells may also be isolated from cultured mesenchymal cells such as fibroblasts or bone mallow mesenchymal cells using the aforementioned isolation means. Furthermore, Muse cells used in the cell preparation of the present invention may be autologous or allogenic relative to the recipient who receives the cell transplant.

As has been described above, although Muse cells or cell populations containing Muse cells can be isolated from biological tissue by using their property of being SSEA-3-positive and CD105-positive, human adult skin is known to contain various types of stem cells and precursor cells. However, Muse cells are not the same as these cells. Examples of such stem cells and precursor cells include skin-derived precursor (SKP) cells, neural crest stem cells (NCSC), melanoblasts (MB), perivascular cells (PC), endothelial precursor (EP) cells and adipose-derived stem cells (ADSC). Muse cells can be isolated from these cells by using "non-expression" of a unique marker as an indicator of these cells. More specifically, Muse cells can be isolated by using non-expression of at least one of 11 markers, such as 1, 2, 3, 4, 5, 6, 7, 8, 9, 10 or 11 markers, selected from the group consisting of CD34 (marker for EP and ADSC), CD117 (c-kit) (MB marker), CD146 (PC and ADSC marker), CD271 (NGFR) (NCSC marker), NG2 (PC marker), vWF factor (von Willebrand factor) (EP marker), Sox10 (NCSC marker), Snail (SKP marker), Slug (SKP marker), Tyrp1 (MB marker) and Dct (MB marker). For example, although not limited thereto, Muse cells can be isolated by using non-expression of CD117 and CD146 as an indicator, can be isolated using non-expression of CD117, CD146, NG2, CD34, vWF and CD271 as an indicator, and can be isolated by using non-expression of the aforementioned 11 markers as an indicator.

In addition, Muse cells having the aforementioned characteristics used in the cell preparation of the present invention may have at least one property selected from the group consisting of:
    (i) low or absent telomerase activity;
    (ii) ability to differentiate into any of the three germ layers;
    (iii) absence of demonstration of neoplastic proliferation; and,
    (iv) self-renewal ability.

In one aspect of the present invention, the Muse cells used in the cell preparation of the present invention have all of the aforementioned properties. Here, with respect to the aforementioned (i), "low or absent telomerase activity" refers to telomerase activity being low or being unable to be detected in the case of having detected telomerase activity using, for example, the Trapeze XL Telomerase Detection Kit (Millipore Corp.). "Low" telomerase activity refers to having telomerase activity roughly equal to that of human fibroblasts, for example, or having telomerase activity that is $1/5$ or less and preferably $1/10$ or less in comparison with Hela cells. With respect to the aforementioned (ii), Muse cells have the ability to differentiate into the three germ layers (endoderm, mesoderm and ectoderm) in vitro and in vivo, and by inducing to differentiate by culturing in vitro, for example, can differentiate into skin, liver, nerve, muscle, bone or fat and the like. In addition, Muse cells may also demonstrate the ability to differentiate into the three germ layers in the case of transplanting in vivo into testes, for example. Moreover, Muse cells also have the ability to migrate, graft and differentiate into a damaged organ (such as the heart, skin, spinal cord, liver or muscle) by being transplanted into the body by intravenous injection. With respect to the aforementioned (iii), although Muse cells proliferate in a suspension culture, they have the property of discontinuing proliferation for about 10~14 days. In adherent culture, their doubling time is approximately 1.3 days/cell division which is similar to human fibroblasts, and keep proliferating until cell reach nearly to Heyflick limit. Thus, in the case of having been transplanted into testes, have the property of not becoming malignant for at least six months. In addition, with respect to the aforementioned (iv), Muse cells have self-renewal (self-replication) ability. Here, "self-renewal" refers to culturing cells contained in an embryoid body-like cell mass obtained by suspension culturing single Muse cell and allowing them to reform an embryoid body-like cell mass from a single cell again as well as to demonstrate spontaneous differentiation of embryoid body-like cell mass into triploblastic cell lineages on gelatin coated culture. Self-renewal may be carried out for one cycle or repeated for a plurality of cycles.

(2) Preparation and Use of Cell Preparation

The cell preparation of the present invention, although not limited thereto, is obtained by suspending Muse cells or a cell population containing Muse cells obtained in the aforementioned (1) in physiological saline or a suitable buffer (such as phosphate-buffered physiological saline). In this case, in the case the number of Muse cells isolated from autologous or allogenic tissue is low, cells may be cultured prior to cell transplant and allowed them to proliferate until a prescribed cell concentration is obtained. Furthermore, as has been previously reported (International Publication No. WO 2011/007900), since Muse cells do not undergo neoplastic transformation, there is little likelihood of the cells becoming malignant even if cells recovered from biological tissue are contained that have still not differentiated, thereby making them safe. In addition, although there are no particular limitations thereon, culturing of recovered Muse cells can be carried out in an ordinary growth medium (such as minimum essential medium-α (α-MEM) containing 10% bovine calf serum). More specifically, a solution containing a prescribed concentration of Muse cells can be prepared by selecting media, additives (such as antibiotics and serum) and the like suitable for the culturing and proliferation of Muse cells with reference to the aforementioned International Publication No. WO2011/007900. In the case of administering the cell preparation of the present invention to a human, roughly several milliliters of bone marrow aspirate are collected from human ilium, and after isolating Muse cells by using an antigen marker for SSEA-3 as an indicator, the cells are allowed to proliferate by culturing for an appropriate amount of time until an effective therapeutic dose is reached, followed by preparing autologous or allogenic Muse cells in the form of a cell preparation. Alternatively, for instance, Muse cells are isolated by using an antigen marker for SSEA-3 as an indicator, and then after the cells are allowed to proliferate by culturing for an appropriate amount of time until an effective therapeutic dose is reached, autologous or allogenic Muse cells can be prepared as a cell preparation.

In addition, when using the cell preparation of Muse cells, dimethylsulfoxide (DMSO) or serum albumin for protecting the cells, or antibiotics and the like for preventing contamination and growth of bacteria, may also be contained in the cell preparation. Moreover, other pharmaceutically allowable components (such as a carrier, vehicle, disintegrating agent, buffer, emulsifier, suspending agent, soothing agent, stabilizer, storage agent, preservative or physiological saline), or cells or components other than Muse cells contained in mesenchymal cells, may also be contained in the cell preparation. A person with ordinary skill in the art is able to add these factors and pharmaceutical agents to a cell preparation at suitable concentrations. In this manner, Muse cells can be used in the form of a pharmaceutical composition containing various types of additives.

The number of Muse cells contained in the cell preparation prepared in the manner described above can be suitably adjusted in consideration of the gender, age and body weight of the subject, disease state and state in which the cells are used so as to obtain the desired effect in treatment of chronic kidney disease (such as improvement of creatinine clearance, reduction of serum creatinine concentration, reduction of blood urea nitrogen, reduction of glomerulosclerosis area). In Examples 3 to 7 to be subsequently described, a mouse model of chronic kidney disease was produced by administration of doxorubicin hydrochloride, and various types of effects of transplanting Muse cells were examined. Extremely superior effects were obtained by administering SSEA3-positive cells to Balb/c mice and SCID mice weighing about 20 g to 30 g at $2 \times 10^4$ cells/animal. On the basis of this result, superior effects can be expected to be obtained by administering 6.6 to $10 \times 10^5$ cells/kg per individual mammal based on body weight. Here, examples of individuals include, but are not limited to, mice and humans. In addition, the cell preparation of the present invention may be administered a plurality of times (such as 2 to 10 times) at a suitable interval (such as twice per day, once per day, twice per week, once per week, once every two weeks, once every one month, one every two months, once every six months) until the desired therapeutic effect is obtained. Thus, although dependent upon the status of the subject, the therapeutically effective dose is preferably administered, for example, 1 to 10 times at $1 \times 10^3$ cells to $1 \times 10^7$ cells per individual. Although there are no particular limitations thereon, examples of total individual doses include $1 \times 10^3$ cells to $1 \times 10^8$ cells, $1 \times 10^4$ cells to $5 \times 10^7$ cells, $2 \times 10^4$ cells to $2 \times 10^7$ cells, $5 \times 10^4$ cells to $5 \times 10^6$, and $1 \times 10^5$ cells to $1 \times 10^6$ cells.

3. Preparation of Mouse Chronic Kidney Disease Model and Therapeutic Effects of Muse Cells In the present description, a mouse chronic kidney disease model can be constructed and used to examine the therapeutic effects of the cell preparation of the present invention on chronic kidney disease. Although there are no particular limitations of the mice of this model, typical examples thereof include Balb/c mice and SCID mice. A chronic kidney disease model can be created by intravenous administration of an anticancer drug (such as doxorubicin hydrochloride) to these mice. Doxorubicin hydrochloride is also known as Adriamycin (common name), and kidney disease (chronic kidney disease resembling human focal glomerular sclerosis) is known to be widely induced by overdosing thereof. According to the present invention, the dosage of doxorubicin hydrochloride is preferably 11.5 µg per kilogram of body weight.

The cell preparation of the present invention has a heterologous relationship with mice administered the preparation since the preparation is derived from Muse cells of human origin. Normally, in experiments in which heterologous cells are administered to model animals, an immunosuppressant (such as cyclosporin) is administered either prior or simultaneous to administration of the heterologous cells in order to suppress an immune response in the body caused by the heterologous cells. The inventors of the present invention have previously found that a population of Muse cells in the form of mesenchymal cells inherently demonstrates potent immunosuppression and that Muse cells have a similar action. Thus, in the present invention, an immunosuppressant is not required to be used in a mouse model in which an immunosuppressant is not used. In actuality, remarkable improvement of renal function attributable to the cell preparation of the present invention was observed without using an immunosuppressant (refer to Examples 1 to 6).

In embodiments of the present invention, the cell preparation of the present invention is able to improve or restore to normal (or normal values) renal function in chronic kidney disease patients. When used in the present description, improvement of renal function refers to alleviation of various symptoms accompanying chronic kidney disease and inhibition of the progression thereof, and preferably refers to alleviation of symptoms to a degree that they do not present a problem during the course of daily life. In addition, returning of renal function to normal refers to returning all symptoms attributable to chronic kidney disease to the state prior to the onset of kidney disease.

Evaluation of renal function of a mouse model following administration of the cell preparation of the present invention can be carried out by using urine protein, creatinine clearance, serum creatinine, blood urea nitrogen (BUN) and urine protein/creatinine ratio, which are generally known and able to be measured easily, as indicators. For example, in the case of measuring creatinine clearance, creatinine originating in muscle tissue is used as an indicator since secretion thereof from renal tubules increases accompanying a decrease in renal function. Thus, creatinine clearance increases as renal function improves or approaches normal, while on the other hand, serum creatinine levels decrease. In addition, blood urea nitrogen (BUN) is a waste product of protein metabolism, and blood BUN levels increase accompanying a decrease in renal function. BUN levels decrease as renal function improves or approaches normal in the same manner as serum creatinine. Furthermore, in humans, the normal range for serum creatinine is 0.4 mg/dl to 1.2 mg/dl, while the normal range for BUN is 8 mg/dl to 20 mg/dl.

Although the following provides a more detailed explanation of the present invention through examples thereof, the present invention is not limited in any way by these examples.

EXAMPLES

Example 1: Preparation of Mouse Chronic Kidney Disease Model

The "Regulations for Animal Experiments and Related Activities at Tohoku University" were strictly observed for the experimental protocol using mice in the present example, and experimental animals were prepared in accordance with these regulations under the supervision of the Tohoku University Experimental Animal Center. More specifically, a mouse chronic kidney disease model was prepared by administering doxorubicin hydrochloride (Sigma Corp.) into a caudal vein of Balb/c mice and SCID mice (males, age 11 to 13 weeks) at 11.5 µg/g of mouse body weight. These animal models presented with a clinical picture resembling focal segmental glomerular sclerosis (FSGS), which is one of the causative diseases of chronic renal failure in humans.

Example 2: Preparation of Human Muse Cells

Preparation of human Muse cells was carried out in accordance with the method described in International Publication No. WO 2011/007900. More specifically, adhesive mesenchymal cells were cultured from human bone marrow fluid and after the cells proliferated, Muse cells or cell populations containing Muse cells were isolated by FACS as SSEA-3-positive cells. In addition, non-Muse cells consisted of a cell group negative for SSEA-3 present among the aforementioned mesenchymal cells, and were used as a control. Subsequently, the cells were adjusted to a prescribed concentration using phosphate-buffered physiological saline or culture liquid, and were used to evaluate the effects of Muse cells on renal function in the chronic kidney disease mouse model as indicated below. Furthermore, in the case of using cells obtained by culturing mesenchymal cells such as bone marrow-derived mesenchymal cells as a population of Muse cells, all SSEA-3-positive cells are known to be CD105-positive cells as reported by Wakao, et al. (2011, ibid).

Example 3: Evaluation of Renal Function in a Balb/c Mouse Chronic Kidney Disease Model by Transplanting Muse Cells The chronic kidney disease mice (Balb/c) prepared in Example 1 were divided into three groups, and Muse cells ($2 \times 10^4$ cells, 200 µl), human bone marrow-derived non-Muse cells ($2 \times 10^4$ cells, 200 µl) or physiological saline (200 µl) were administered into a caudal vein of mice in each group one week after administration of doxorubicin hydrochloride. Subsequently, after allowing the passage of a prescribed amount of time, creatinine clearance, serum creatinine, blood urea nitrogen (BUN) and urine protein were measured in accordance with ordinary methods for each mouse followed by evaluation of the therapeutic effects of Muse cells on the chronic kidney disease mice. Furthermore, although all of the cells used for administration were of human origin, an immunosuppressant was not used throughout the experimental period when the cells were administered to the mice.

(a) Creatinine Clearance and Serum Creatinine

The results of measuring creatinine clearance (µl/min) for each of the aforementioned mouse model groups six weeks after administering doxorubicin hydrochloride are shown on the left side of FIG. 1. Creatinine clearance in the Muse cell dose group was significantly higher in comparison with the non-Muse cell dose group and physiological saline dose group. Significant differences were observed between the Muse cell dose group and the non-Muse cell and physiological saline dose groups, respectively. As a result, the function of excreting serum creatinine was determined to have recovered in the kidneys of chronic kidney disease mice administered Muse cells. Moreover, serum creatinine concentration (mg/dl) was measured for each of the aforementioned mouse model groups (right side of FIG. 1). Serum creatinine concentrations in the Muse cell dose group were lower in comparison with the physiological saline dose group, demonstrating a statistically significant difference therewith. On the other hand, the non-Muse cell dose group did not demonstrate a statistically significant difference when compared with the physiological saline dose group.

(b) Blood Urea Nitrogen (BUN) and Urine Protein/Creatinine Ratio

Figure 2:
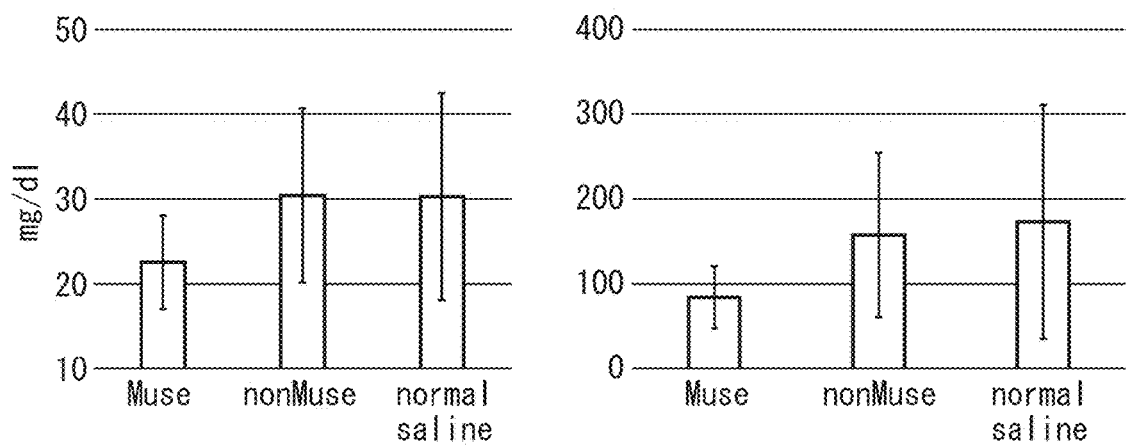
FIG. 2 indicates the results of evaluating renal function in a chronic kidney disease mouse (Balb/c) model six weeks after transplanting human Muse cells. The graph on the left indicates the results for blood urea nitrogen (BUN), while the graph on the right indicates the results for urine protein/creatinine ratio. In a dose group administered Muse cells, blood urea nitrogen concentration decreased in comparison with dose groups administered non-Muse cells and physiological saline. Moreover, when the urine protein/creatinine ratio in voided urine was measured, the ratio in the Muse cell dose group was low in comparison with the other groups and renal function was suggested to have improved.

Blood urea nitrogen (BUN) concentration (mg/dl) was measured six weeks after administration of doxorubicin hydrochloride in order to investigate urine excretory function of the kidneys. As shown on the left side of FIG. 2, blood urea nitrogen concentrations decreased in the Muse cell dose group in comparison with the non-Muse cell dose group and physiological saline dose group. Moreover, when urine protein/creatinine ratio was measured in voided urine, this ratio was lower in the Muse cell dose group in comparison with the other groups, and renal function was suggested to be improved (right side of FIG. 2).

(c) Glomerular Sclerosis

Figure 3:
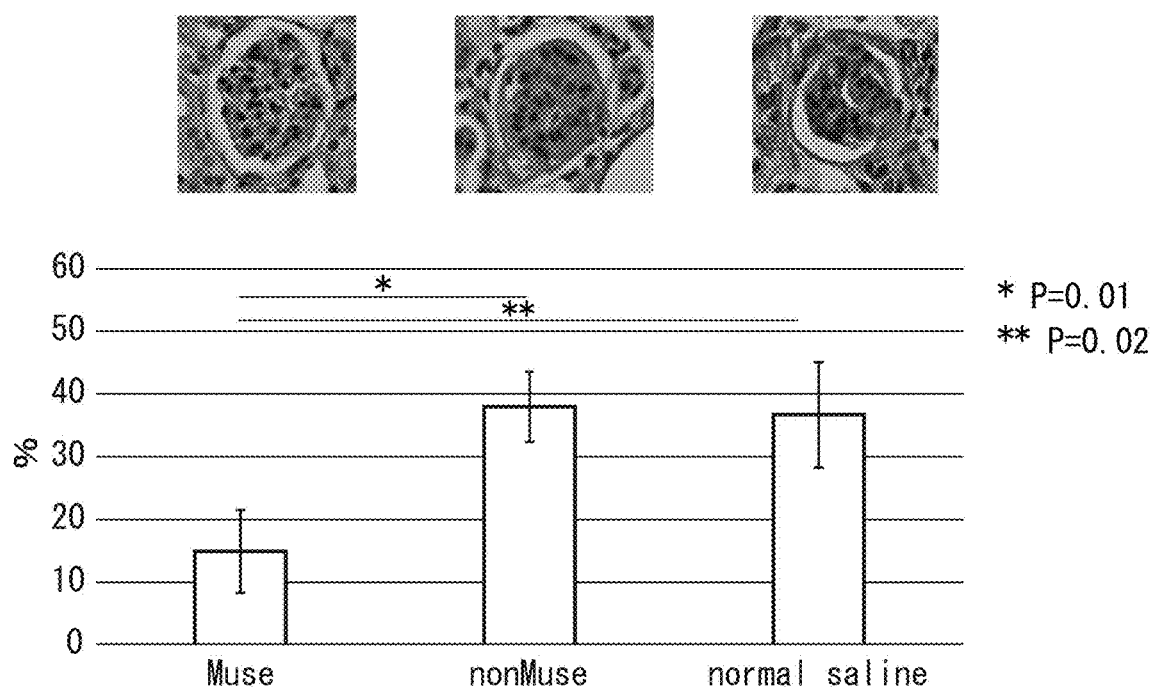
FIG. 3 indicates the results of examining glomerular repair effects of human Muse cells on glomerular sclerosis accompanying chronic kidney disease (after six weeks). The images at the top of the drawing indicate renal tissue sections stained with PAS, and respectively indicate, moving from left to right, a Muse cell dose group, non-Muse cell dose group and physiological saline group. In the Muse cell dose group, the glomerular basement membrane was extremely well-defined. On the other hand, in the non-Muse cell group and physiological saline group, glomerular sclerosis had progressed and the contour of the glomerular basement membrane was indistinct. Moreover, 20 glomeruli per individual were consecutively observed for individuals from each group, and the area ratio of glomerular sclerosis was analyzed using NIS Elements™ image analysis software (Nikon Corp.) to determine the PAS positive area per glomerulus (bottom of drawing). In the Muse cell dose group, the area ratio of glomerular sclerosis was small in comparison with other dose groups. As a result, Muse cells were suggested to prevent progression of glomerular sclerosis as well as promote reconstruction and repair of the glomerulus.

The glomerular repair effects of Muse cells on glomerular sclerosis accompanying chronic kidney disease were examined six weeks after administration of doxorubicin hydrochloride (FIG. 3). Each mouse was sacrificed followed by preparing renal tissue sections and staining the sections with PAS. As a result of this staining, the degree of glomerular sclerosis was observed from changes in the glomerular basement membrane. The top of FIG. 3 indicates renal tissue (glomerulus) sections of each mouse in the Muse cell, non-Muse cell and physiological saline dose groups. In the Muse cell dose group (left side), the glomerular basement membrane can be seen to be extremely well-defined. On the other hand, in the non-Muse cell dose group and physiological saline dose group (center and right side), glomerular sclerosis has progressed and the contour of the glomerular basement membrane is indistinct. Moreover, 20 glomeruli per individual were consecutively observed for individuals from each model group, and the area ratio of glomerular sclerosis was analyzed using NIS Elements' image analysis software (Nikon Corp.) to determine the PAS positive area per glomerulus (bottom of drawing). In the Muse cell dose group, the area ratio of glomerular sclerosis was small in comparison with the other dose groups. As a result, Muse cells were suggested to prevent progression of glomerular sclerosis as well as promote reconstruction and repair of the glomerulus.

Figure 4:
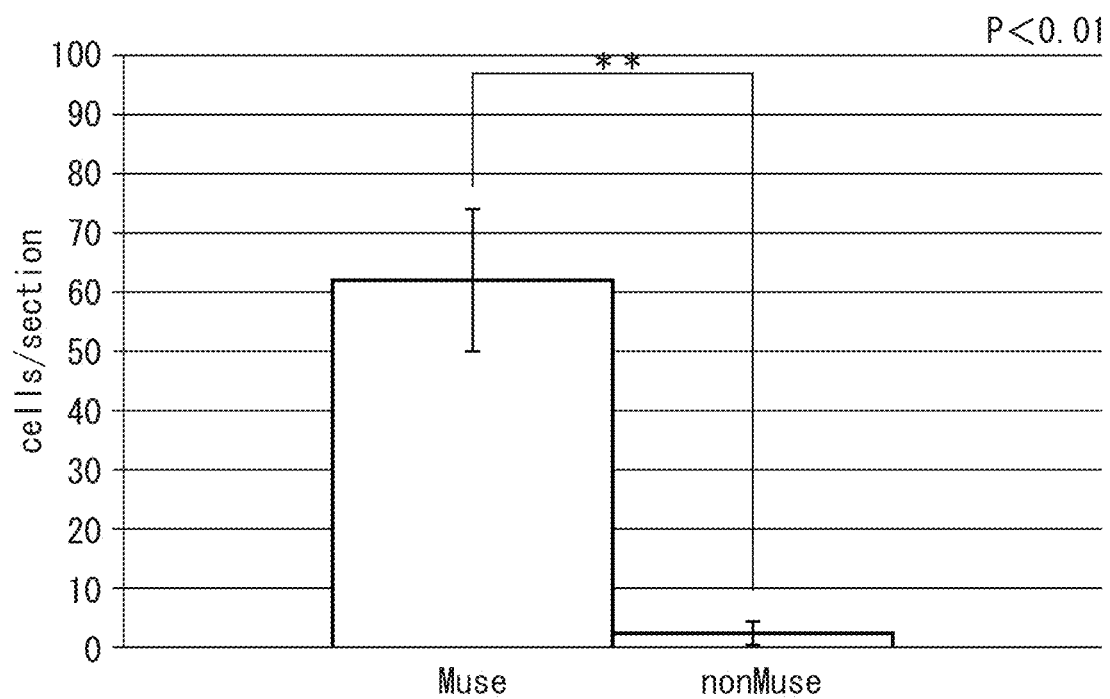
FIG. 4 indicates the results of examining the taking of human Muse cells and non-Muse cells to renal tissue following administration into a caudal vein (after six weeks). In contrast to Muse cells having taken to renal tissue, hardly any of the non-Muse cells took to renal tissue.

Example 4: Taking and Differentiation of Muse Cells in Renal Tissue (a) Taking of Muse Cells to Renal Tissue A study was conducted as to whether or not Muse cells take to renal tissue in order to investigate the behavior of Muse cells and non-Muse cells administered via a caudal vein. First, GFP-positive Muse cells and non-Muse cells were prepared, and renal tissue sections were prepared in the same manner as Example 3 using mice administered these cells for 8 weeks followed by observing the tissue sections under a fluorescence microscope. The number of transplanted cells was counted per unit area to examine taking of the Muse cells and non-Muse cells. As shown in FIG. 4, in contrast to the administered Muse cells having taken to renal tissue, hardly any of the non-Muse cells took to renal tissue.

Figure 5:
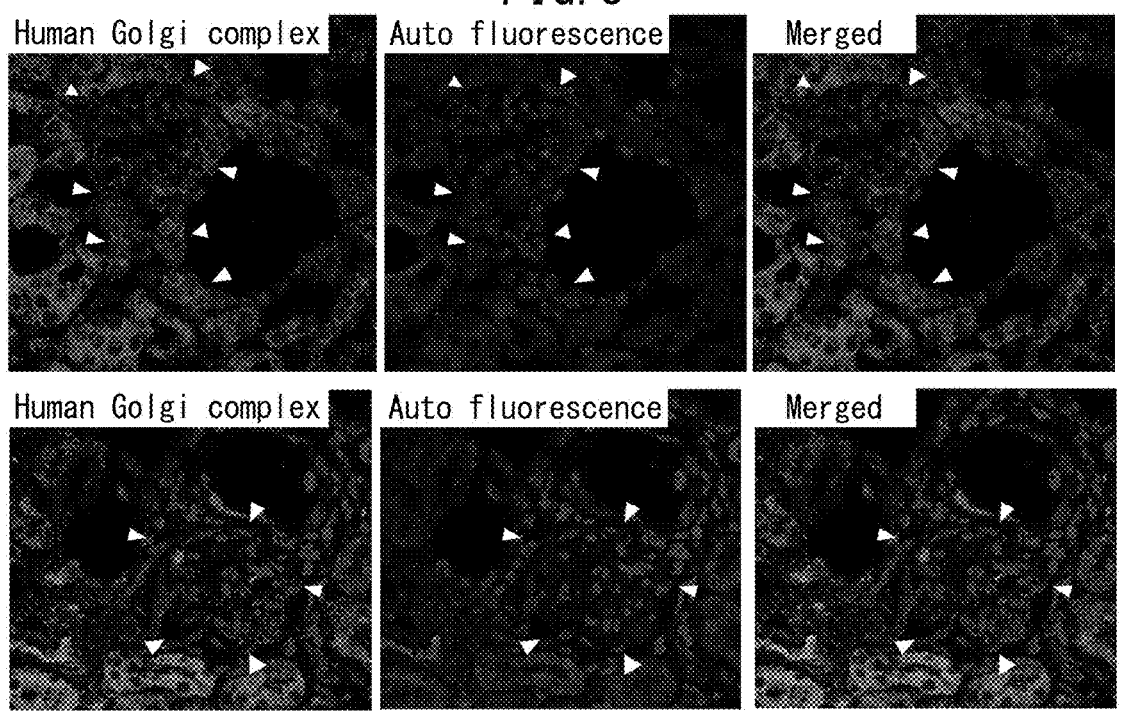

Next, GFP-positive, non-labeled human Muse cells were administered, and after preparing renal tissue sections in the same manner as Example 3 8 weeks later, the human Muse cells were stained using anti-human Golgi complex antibody. FIG. 5 shows fluorescent images of regions containing a single glomerulus and the periphery thereof. Although the left panels of FIG. 5 depict fluorescent images in the case of staining with the antibody, since renal tissue demonstrates intense autofluorescence as shown in the center panels, fluorescent images obtained by subtracting autofluorescence from the antibody-induced fluorescence are shown in the right panels. The upper fluorescent images are images obtained from the Muse cell dose group, and as indicated by the arrows, Muse cells were widely distributed and took to glomeruli, renal tubules, interstitium and the like.

(b) Differentiation of Muse Cells in Renal Tissue

Figure 6:
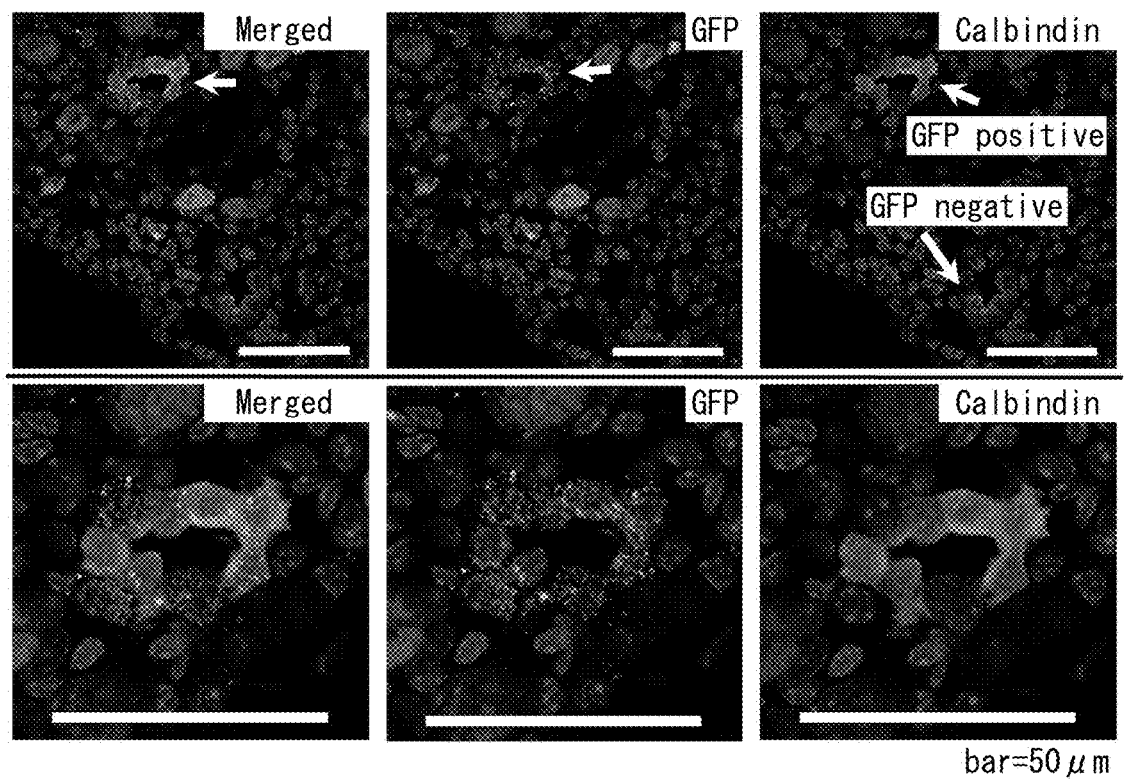
FIG. 6 indicates the results of examining differentiation of human Muse cells that had taken to mouse renal tissue. Green fluorescent protein (GFP)-positive human Muse cells were used that had been introduced with GFP gene. In addition, the cells were fluorescence-stained using antibody to calbindin that is specifically expressed in epithelial cells of distal renal tubules. The center panels indicate Muse cells that had taken to distal renal tubules (GFP positive). The right panels indicate epithelial cells specified by antibody to calbindin. The left panels indicate images obtained by superimposing these images. Since GFP fluorescence and calbindin fluorescence are observed in the same cell group when regions of particularly intense fluorescence are enlarged, Muse cells were suggested to accumulate in and take to distal renal tubules and differentiate into distal renal tubules.
Figure 7:
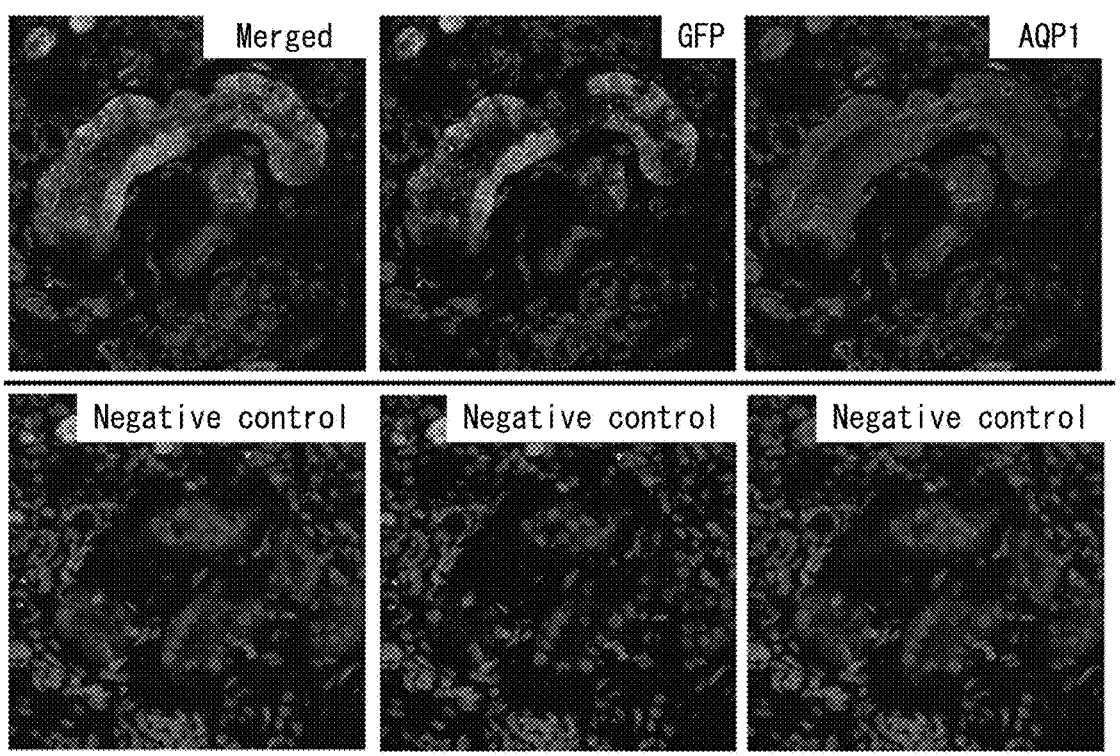
FIG. 7 indicates the results of examining differentiation of human Muse cells that had taken to mouse renal tissue. GFP-positive human Muse cells were used in the same manner as FIG. 6 (center panel). In addition, fluorescence staining was carried out using antibody to aquaporin (AQP1) that is specifically expressed in the epithelial cells of proximal renal tubules (right panel). Images obtained by superimposing these images are indicated in the left panel. On the basis of these results, since GFP fluorescence and AQP1 fluorescence were observed within the same cell group, human Muse cells were suggested to accumulate in and take to proximal renal tubules and differentiate into epithelial cells. Furthermore, cells that were not stained with primary antibody to GFP and AQP1 were used as negative controls (bottom row).

A study was conducted as to whether or not Muse cells that had taken to renal tissue differentiate. In this experiment, green fluorescent protein (GFP)-positive Muse cells were used that were introduced with GFP gene. In addition, differentiation of Muse cells into epithelial cells was examined using antibody to calbindin specifically expressed in epithelial cells of distal renal tubules. The center panels of FIG. 6 indicate Muse cells (GFP-positive) that took to distal renal tubules. On the other hand, the left panels of FIG. 6 indicate epithelial cells obtained by antibody staining to calbindin. Images obtained by superimposing these images are shown in the right panels of FIG. 6. Since GFP fluorescence and calbindin fluorescence were observed in the same cell group when regions of particularly intense fluorescence were enlarged, Muse cells were suggested to accumulate in distal renal tubules and differentiate into distal renal tubule cells. Moreover, a study was conducted as to whether or not Muse cells take to proximal renal tubules and differentiate into epithelial cells of proximal renal tubules based on expression of aquaporin (AQP1). The top row of images in FIG. 7 consists of GFP fluorescent images in the case of having administered Muse cells (center panel), images obtained by AQP1 staining (right panel), and images obtained by superimposing the two (left panel). As can be understood from the superimposed images, since GFP-positive Muse cells express a molecular marker of proximal renal tubule epithelial cells in the form of aquaporin, the administered Muse cells were suggested to accumulate in proximal renal tubules and differentiate into proximal renal tubule cells. Furthermore, cells not stained with primary antibody to GFP and AQP1 were used as negative controls (bottom row in FIG. 7).

Example 5: Examination of Migration Ability of Muse Cells

Figure 8:
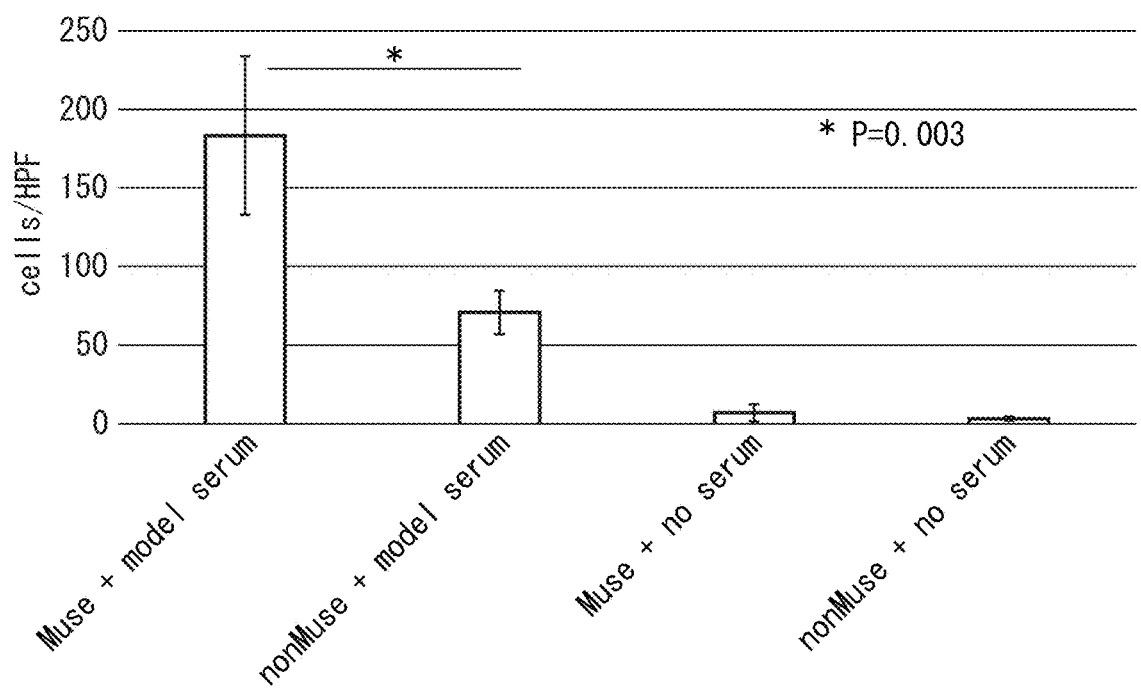
FIG. 8 indicates the results of examining the migration ability of human Muse cells. The Boyden chamber method was used to evaluate migration ability. Hardly any cells were observed to pass through inserts in a system containing human Muse cells but not containing disease model mice serum or in a system containing non-human Muse cells but not containing disease model mice serum. In contrast, in a system to which was added disease model mice serum, Muse cells demonstrated extremely high migration, and this migration was prominent in comparison with conditions consisting of non-Muse cells combined with disease model mice serum. On the basis thereof, the disease model mice serum was suggested to contain some type of factor for inducing migration of Muse cells.

As was described above, Muse cells administered into a caudal vein of chronic kidney disease model mice were suggested to accumulate at sites of kidney disease and greatly contribute to reconstruction and repair of glomeruli, distal renal tubules and proximal renal tubules. Next, a study was made of the migration ability of Muse cells in vitro according to the Boyden chamber method with respect to accumulation of Muse cells at sites of kidney disease. More specifically, the BD Matrigel™ Invasion Chamber (BD Bioscience-Discovery Labware Inc.) was used for the Boyden chamber, and the chamber contained BD Falcon Cell Culture Inserts having a pore size of 8.0 μm. Matrigel Matrix was applied to the upper surface of the inserts. Serum from the disease model mice was added to the lower portion of the inserts and the inserts were then inoculated with Muse cells ($3.5\times10^4$ cells/well) or non-Muse cells ($3.5\times10^4$ cells/well). After culturing for 20 hours, the number of cells that passed through the inserts was determined under a microscope. The results are shown in FIG. 8. The number of cells present per field as observed with the high power field of a microscope is plotted on the vertical axis. Hardly any cells were observed to pass through the inserts in a system containing human Muse cells but not containing disease model mice serum or in a system containing non-human Muse cells but not containing disease model mice serum. In contrast, in a system to which was added disease model mice serum, Muse cells demonstrated extremely high migration, and this migration was prominent in comparison with conditions consisting of non-Muse cells combined with disease model mice serum. On the basis thereof, the disease model mice serum was suggested to contain some type of factor for inducing migration of Muse cells.

Example 6: In Vivo Cell Mobility Assay

Figure 9:
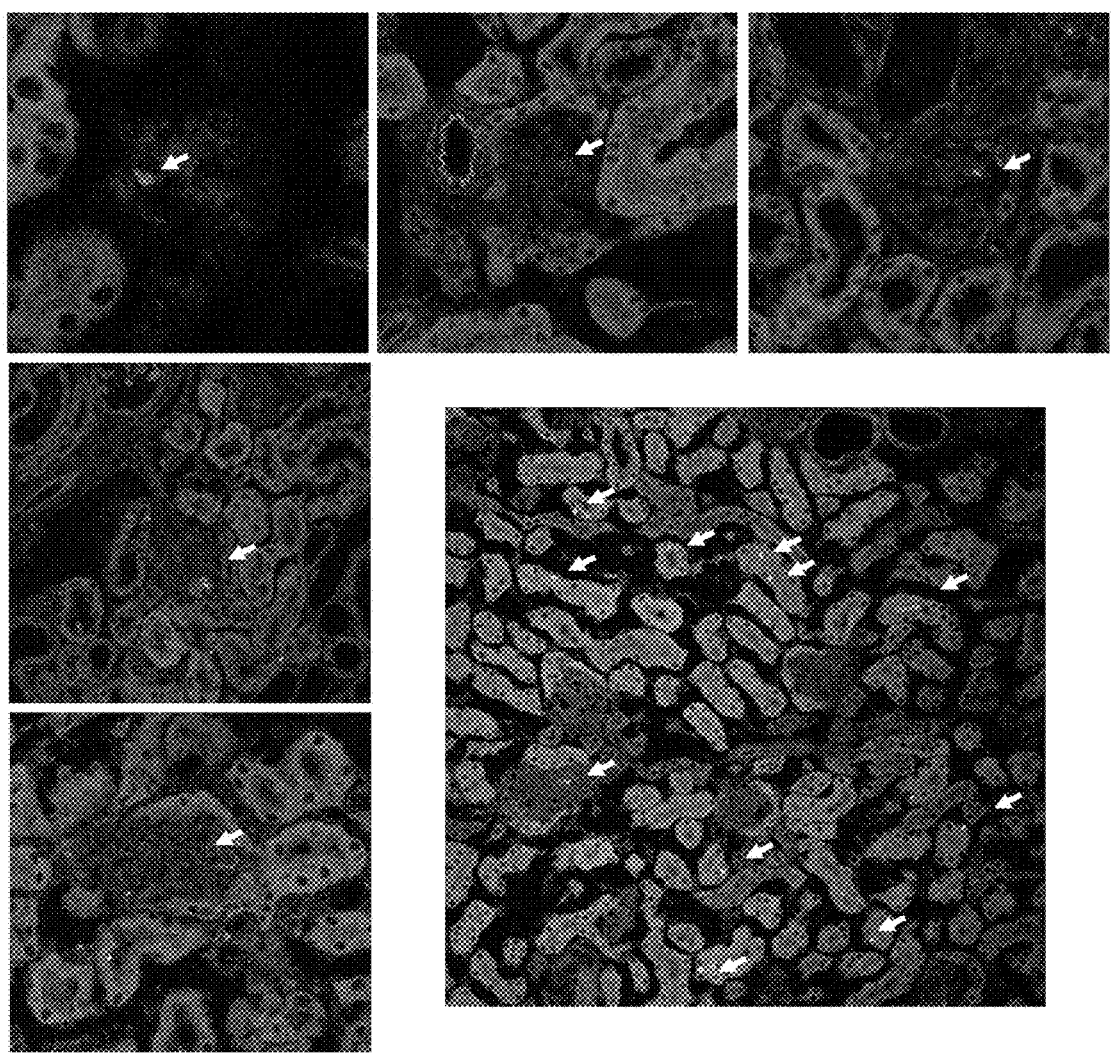
FIG. 9 indicates the results of examining the mobility of human Muse cells to sites of kidney disease. Muse cells stained with Hoechst 33342 stain were administered into a caudal vein of chronic kidney disease model mice, followed by fixing the renal tissue and observing under a fluorescence microscope 24 hours later. Nuclear-stained Muse cells were identified as spots exhibiting a strong signal (indicated by arrows). Muse cells administered into a caudal vein can be understood to be widely distributed in, for example, glomeruli, renal tubules and interstitium.

A study was made of the mobility of Muse cells to sites of kidney disease in a chronic kidney disease mouse model. Muse cells and non-Muse cells were respectively adhered to a culture dish, and after culturing overnight, the cell nuclei thereof were stained with Hoechest 33342 stain (Sigma Corp.). Continuing, after treating the cells with trypsin, the cells were counted and $2\times10^4$ cells were administered into a caudal vein of the chronic kidney disease model mice. Renal tissue was fixed in accordance with ordinary methods 24 hours after administration and observed under a fluorescence microscope. Fluorescent images obtained following administration of Muse cells are shown in FIG. 9, while fluorescent images obtained following administration of non-Muse cells are shown in FIG. 10. In all of these images, nuclei of the stained Muse cells and non-Muse cells were identified as spots exhibiting a strong signal (indicated by arrows). Although Muse cells administered into a caudal vein were widely distributed in glomeruli, renal tubules, interstitium and the like, non-Muse cells were only observed in renal tubules and interstitium. On the basis thereof, Muse cells are thought to have potent abilities to migrate and take to disease sites in comparison with non-Muse cells.

Figure 11:
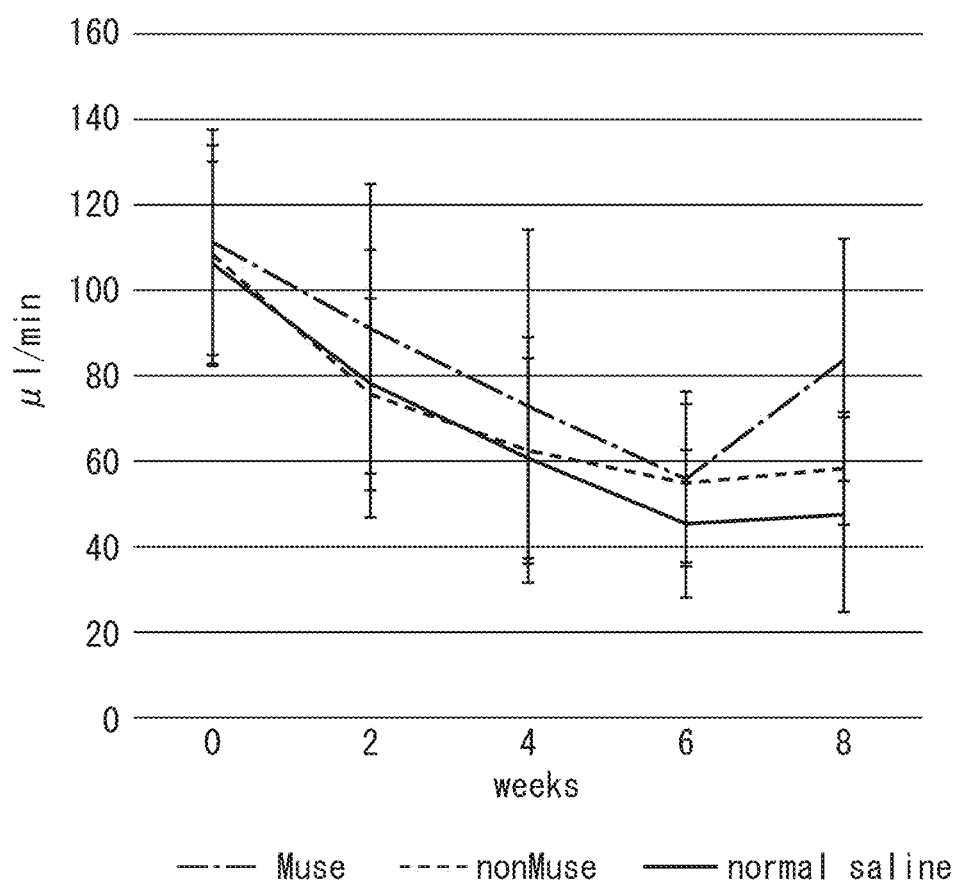
FIG. 11 indicates the results of measuring time-based changes in creatinine clearance (µl/min) resulting from transplantation of human Muses cells in a chronic kidney disease model using SCID mice. Creatinine clearance was significantly higher in the Muse cell dose group in comparison with the non-Muse cell dose group and physiological saline dose group, and renal function was suggested to have recovered considerably.

Example 7: Evaluation of Renal Function in SCID Mouse Chronic Kidney Disease Model by Transplanting Human Muse Cells and Taking and Differentiation of Muse Cells in Renal Tissue One of the parameters for evaluating renal function in the form of creatinine clearance was measured over time using immunodeficient SCID mice that do not reject human cells. The experimental procedure consisted of dividing the chronic kidney disease mice (SCID) prepared in Example 1 into three groups, and administering Muse cells ($2\times10^4$ cells, 200 μl), human bone marrow-derived non-Muse cells ($2\times10^4$ cells, 200 μl) or physiological saline (200 μl) into a caudal vein of mice in each group one week after administration of doxorubicin hydrochloride in the same manner as Example 3. Subsequently, creatinine clearance was measured for each mouse over time, and the results are shown in FIG. 11. Although creatinine clearance in the human Muse cell dose group decreased from the start of measurement through week 6, during the measurement period, values were significantly higher in comparison with the non-Muse cell and physiological saline dose groups. In addition, renal function was suggested to be restored considerably in the Muse cell dose group in the same manner as in the Balb/c mouse chronic kidney disease model.

Figure 12:
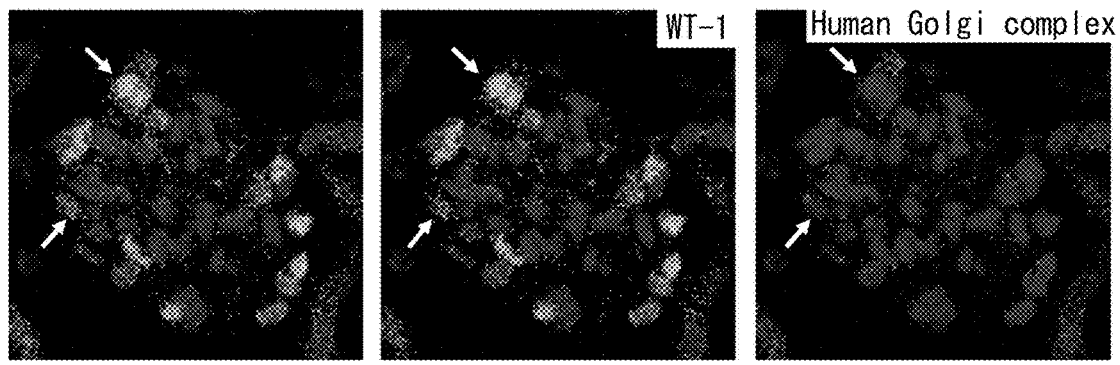
FIG. 12 indicates fluorescent images obtained in regions containing a single glomerulus and the periphery thereof following transplantation of human Muse cells (8 weeks after administration of doxorubicin hydrochloride). In the left panel, Muse cells that had taken to mouse kidney were detected using anti-human Golgi complex antibody. The center panel indicates a fluorescent image indicating podocytes detected using antibody to a podocyte marker in the form of WT-1 (transcription factor). The right panel indicates an image obtained by superimposing both fluorescent images, and since fluorescence of human Golgi complex antibody and WT-1 was observed within the same cell group, the administered Muse cells were suggested to accumulate in the glomerulus and differentiate into podocytes.
Figure 13:
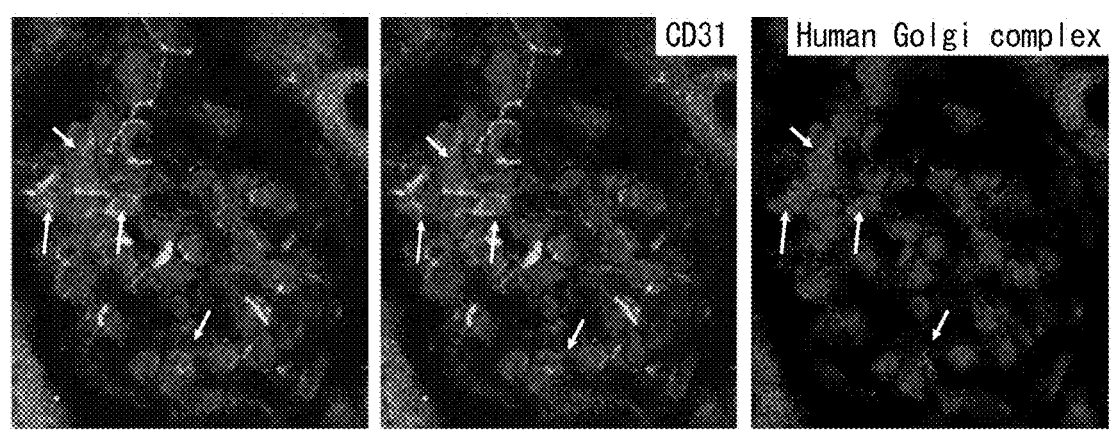
FIG. 13 suggests that, when immunofluorescence staining is carried out using antibody to a surface antigen marker of vascular endothelial cells in the form of CD31, administered Muse cells differentiate into vascular endothelial cells in the glomerulus. The right panel indicates human Muse cells that were immunofluorescent-stained using anti-human Golgi complex antibody, the center panel indicates vascular endothelial cells subjected to immunofluorescence staining using antibody to CD31, and the right panel indicates the results of superimposing both images.

Moreover, a study was conducted as to whether or not Muse cells take to and differentiate into renal tissue in order to investigate the behavior of Muse cells administered to SCID mice. Renal tissue sections were prepared in the same manner as Example 3 in week 8 after administration of Muse cells, and in the present example in particular, an investigation was conducted as to whether or not Muse cells take to glomeruli by fluorescence staining. As shown in FIG. 12, Muse cells exhibited red fluorescence by antibody to human Golgi complex (right panel), and when expression of a known podocyte marker in the form of WT-1 (transcription factor) was detected using antibody thereto, the Muse cells exhibited green fluorescence (center panel). In an image obtained by superimposing both panels (left panel), since fluorescence attributable to human Golgi complex antibody and WT-1 were observed in the same cell group, the administered Muse cells were suggested to accumulate in glomeruli and differentiate into podocytes. Moreover, when the Muse cells were immunofluorescence-stained using antibody to a surface antigen marker of intravascular endothelial cells in the form of CD31, the administered Muse cells were suggested to differentiate to vascular endothelial cells in glomeruli (FIG. 13). In this manner, the administered Muse cells were suggested to have the potential to accumulate at disease sites and differentiate into cells that compose renal tissue even in SCID mice of a chronic kidney disease model.

INDUSTRIAL APPLICABILITY

The cell preparation of the present invention can be applied to the treatment of chronic kidney disease since it is able to induce reconstruction and repair of renal tissue at the site of kidney disease as well as restore renal function by being administered to chronic kidney disease model mice.

All publications and patent documents cited in the present description are incorporated throughout the description by reference. Furthermore, although specific embodiments of the present invention have been explained in the present description for the purpose of exemplification, it can be easily understood by a person with ordinary skill in the art that the present invention may be modified in various ways without departing from the spirit and scope thereof.

What is claimed is:

1. A method for treating chronic kidney disease in a mammalian subject having damaged renal tissue, the method comprising: administering a cell preparation comprising an effective amount of human pluripotent stem cells positive for SSEA-3 isolated from biological mesenchymal tissue or cultured mesenchymal cells, wherein the human pluripotent stem cells have been concentrated, said human pluripotent stem cells having a plurality of properties, said plurality of properties comprising:
  (i) CD105-positively;
  (ii) low or absent telomerase activity;
  (iii) ability to differentiate into any of the three germ layers;
  (iv) absence of demonstration of neoplastic proliferation; and
  (v) self-renewal ability;
  wherein the human pluripotent stem cells migrate to and accumulate in the damaged renal tissue, wherein upon accumulation said human pluripotent stem cells differentiate into cells constituting renal tissue to thereby treat the chronic kidney disease, wherein the chronic kidney disease is treated on the basis of repression of progression of the chronic kidney disease and improvement of kidney function by means of a renal tissue regeneration mechanism, wherein the chronic kidney disease is selected from the group consisting of chronic glomerular nephritis, renal sclerosis, diabetic nephropathy, renal cyst, chronic pyelonephritis, rapidly progressive glomerulonephritis, malignant hypertension, SLE nephritis, renal amyloidosis, renal/urinary tract tumors, myeloma, obstructive uropathy, renal gout, renal hypoplasia and renal/urinary tract tuberculosis.

2. The method according to claim 1, wherein the human pluripotent stem cells positive for SSEA-3 contain a concentrated cell fraction as a result of stimulation by external stress.

3. The method according to claim 1, wherein the human pluripotent stem cells are CD117-negative and CD146-negative.

4. The method according to claim 1, wherein the human pluripotent stem cells are CD117-negative, CD146-negative, NG2-negative, CD34-negative, vWF-negative and CD271-negative.

5. The method according to claim 1, wherein the human pluripotent stem cells are CD34-negative, CD117-negative, CD146-negative, CD271-negative, NG2-negative, vWF-negative, Sox10-negative, Snail-negative, Slug-negative, Tyrp1-negative and Dct-negative.

6. The method according to claim 1, wherein the human pluripotent stem cells have the ability to differentiate into one or more cells selected from the group consisting of foot cells, mesangium cells, glomerular endothelial cells, juxtaglomerular cell, proximal tubular cells, distal tubular cells, vascular endothelial cells, Henle's loop, and collecting tubule cells.

7. The method according to claim 1, wherein the chronic kidney disease of a kidney having a damaged glomerulus is treated on the basis of prevention of progression of glomerular sclerosis and promotion of reconstruction and repair of the glomerulus.

* * * * *